United States Patent
Eckhouse et al.

(10) Patent No.: US 6,471,692 B1
(45) Date of Patent: *Oct. 29, 2002

(54) SYSTEM AND METHOD FOR MANIPULATING MOVEMENT OF AN ENERGY EMITTING DEVICE WITHIN A BODY CAVITY

(75) Inventors: Shimon Eckhouse, Haifa; Rafi Rabinowitz, Raanana; Ziv Karni, Kfar Shmaryahu; Uri Levy, Rehovot, all of (IL)

(73) Assignee: Laser Industries Ltd., Tel-Aviv (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/103,609
(22) Filed: Jun. 24, 1998
(51) Int. Cl.[7] ............................... A61B 18/18
(52) U.S. Cl. ..................... 606/15; 606/14; 607/89
(58) Field of Search ................ 606/1, 14, 15, 606/16, 17, 9, 10, 11, 12; 607/88, 89

(56) References Cited

U.S. PATENT DOCUMENTS

| | | | |
|---|---|---|---|
| 3,858,577 A | 1/1975 | Bass et al. | |
| 4,249,533 A | 2/1981 | Komiya | |
| 4,266,547 A | 5/1981 | Komiya | |
| 4,313,431 A | 2/1982 | Frank | |
| 4,790,310 A | 12/1988 | Ginsburg et al. | |
| 4,791,926 A | * 12/1988 | Fry | 606/15 |
| 4,799,479 A | 1/1989 | Spears | |
| 4,800,876 A | 1/1989 | Fox et al. | |
| 4,913,142 A | 4/1990 | Kittrell et al. | |
| 4,998,930 A | 3/1991 | Lundahl | |
| 5,078,711 A | * 1/1992 | Kakami et al. | 606/15 |
| 5,112,328 A | 5/1992 | Taboada et al. | |
| 5,156,604 A | * 10/1992 | Hessel et al. | 606/15 |
| 5,169,396 A | 12/1992 | Dowlatshahi et al. | |
| 5,188,634 A | 2/1993 | Hussein et al. | |
| 5,188,635 A | 2/1993 | Radtke | |
| 5,217,454 A | 6/1993 | Khoury | |
| 5,222,953 A | * 6/1993 | Dowlatshahi | 606/15 |
| 5,298,026 A | 3/1994 | Chang | |
| 5,354,296 A | 10/1994 | Turkel | |
| 5,401,270 A | 3/1995 | Muller et al. | |
| 5,419,312 A | 5/1995 | Arenberg et al. | |
| 5,449,354 A | 9/1995 | Komwitz et al. | |
| 5,454,782 A | * 10/1995 | Perkins | 606/15 |
| 5,458,595 A | * 10/1995 | Jadir et al. | 606/15 |
| 5,469,524 A | * 11/1995 | Esch et al. | 606/15 |
| 5,486,170 A | * 1/1996 | Winston et al. | 606/15 |
| 5,500,012 A | 3/1996 | Brucker et al. | |
| 5,549,601 A | * 8/1996 | McIntyre et al. | 606/15 |
| 5,603,710 A | * 2/1997 | Easley et al. | 606/4 |
| 5,620,478 A | 4/1997 | Eckhouse | |
| 5,651,785 A | * 7/1997 | Abela et al. | 606/8 |
| 5,703,985 A | 12/1997 | Owyang | |
| 5,733,277 A | * 3/1998 | Pallarito | 606/7 |
| 5,733,279 A | 3/1998 | Konwitz et al. | |
| 5,776,129 A | 7/1998 | Mersch | |
| 5,800,379 A | * 9/1998 | Edwards | 604/22 |
| 5,876,373 A | * 3/1999 | Giba et al. | 604/95 |
| 5,897,551 A | * 4/1999 | Everett et al. | 606/15 |
| 6,058,323 A | * 5/2000 | Lemelson | 600/48 |
| 6,113,589 A | * 9/2000 | Levy et al. | 606/16 |
| 6,135,996 A | * 10/2000 | Kolesa et al. | 606/15 |

FOREIGN PATENT DOCUMENTS

| | | |
|---|---|---|
| WO | WO 94/00061 | 1/1994 |
| WO | WO 96/06574 | 3/1996 |

* cited by examiner

*Primary Examiner*—Roy Gibson
(74) *Attorney, Agent, or Firm*—Eitan, Pearl, Latzer & Cohen-Zedek

(57) ABSTRACT

A system and a method for manipulating movement within a body cavity. The device includes an optical fiber coupled to an energy source and a sleeve for containing the fiber. The fiber has distal end for positioning adjacent to a surface being treated within the body cavity and a proximal end located external to the body cavity which is coupled to an operating device for controlling the lateral and/or longitudinal movement of the fiber.

1 Claim, 4 Drawing Sheets

SYSTEM AND METHOD FOR MANIPULATING MOVEMENT OF AN ENERGY EMITTING DEVICE WITHIN A BODY CAVITY

FIELD OF THE INVENTION

The present invention relates to an apparatus for treating and/or viewing the interior of a body cavity with an energy emitting device, to an apparatus for manipulating the movement of said energy emitting device and to a system and method including same.

BACKGROUND OF THE INVENTION

A number of applications are known in the art in which a light emitting device is introduced into a body cavity for treatment and/or viewing of the body cavity. One example is the uterus where excessive and/or prolonged menstrual bleeding (or chronic menorrhagia) is traditionally treated by birth control pills, other hormonal therapies, or by a minor operation called "D and C" (dilation and curettage) involving a scraping of the lining of the uterus. When such treatments are not effective, a hysterectomy is generally performed which involves removing the uterus and the lining along with it. Approximately 600,000 hysterectomies are performed in the USA each year.

An alternative method of tissue destruction is known as interstitial thermo-therapy (ITT). In this method, the tissue temperature is elevated above a certain threshold temperature for a certain duration by absorption of light. Light, in turn, is transmitted to the scene via an optical fiber and is scattered and diffused to be absorbed by the volume of tissue to be destroyed. Usually, the light source is a laser, such as a Nd:YAG laser system or Diode laser system.

Recently, a technique has been developed using laser energy to ablate the uterine lining such as to cause scarring that prevents the lining from growing back. In this technique, a laser beam is conducted into the uterus by means of an optical fiber. The optical fiber is inserted via a channel of a hysteroscope, enabling the physician to view the interior of the uterus as the physician manipulates the tip of the optical fiber. The physician sweeps the tip of the optical fiber across the uterine lining to ablate the lining to a depth of about 3–5 mm. This procedure is carried out under general anesthesia by a skilled operator, is time consuming and there is a risk of uterine perforation.

An alternative technique is to slowly and simultaneously elevate the temperature of the whole surface being treated. This is carried out by scattering light from the optical fibers. The fibers used for transmitting and diffusing the laser light are generally known as induced interstitial thermotherapy (ITT) fibers.

ITT fibers are well known. An example of an optical device which uses ITT fibers is described in U.S. Pat. No. 5,449,354, incorporated herein by reference, which discloses a device for treating the interior of a body cavity with laser energy particularly useful for the procedure. The described apparatus comprises at least two optical fibers each having a distal end adapted to be inserted into the body cavity to be treated, and a proximal end to be located externally of the body cavity and to be coupled to a source of laser energy. One of the optical fibers is axially movable with respect to the other optical fiber to either a retracted, non-operative position or to an extended, operative position. The distal ends of the two optical fibers are mechanically coupled together such that movement of one optical fiber axially with respect to the other causes the distal ends of the two optical fibers to spread apart laterally, and to direct the laser energy outwardly of the optical fibers.

In the preferred embodiment described in that patent application, the optical fibers are disposed within a cannula having a distal end adapted to be inserted into the body cavity to be treated, and a proximal end to be located externally of the body cavity when the distal end is inserted therein. In the described device, there were three optical fibers within the cannula arranged in side-by-side relation, with two of the fibers being outer fibers, and the third fiber being the middle fiber straddled on opposite sides by the two outer fibers. The two outer fibers are axially movable with respect to the middle fiber, and the distal ends of the three fibers are mechanically coupled together such that movement of the two outer fibers axially with respect to the middle fiber causes the distal ends of all three fibers to spread apart laterally.

As described in U.S. Pat. No. 5,449,354, such a laser device is particularly useful for treating chronic menorrhagia since a single dosage of laser energy will substantially cover most or all of the uterine lining. Thus, the device avoids the need for the physician to view the interior of the uterus, and thereby the need for inserting a hysteroscope into the uterus. In addition, it reduces the dilation required of the uterus, and also substantially reduces the time of treatment. Local anesthesia can be used and the procedure can be carried out with minimal training at lower risk to the patient.

U.S. Pat. No. 5,733,279 incorporated herein by reference, discloses a further device for treating the interior of a body cavity with laser energy without the need for a cannula, thereby reducing the dilation required of the uterus during treatment. The apparatus describes a device having at least two outer fibers and a middle fiber, in side-by-side relation each having a distal end to be inserted into the body cavity to be treated, and a proximal end to be located externally of the body cavity and to be coupled to a source of laser energy, and actuator means coupled to the optical fibers. In the preferred embodiment described in that patent application, the actuator means comprises rods for coupling each of the outer fibers to the middle fiber, one end of the rods is pivotally connected to each of the distal ends of the outer fibers and the other end is pivotally connected to the middle fiber. This arrangement allows for manually activating the proximal end of the outer fibers to move axially with respect to the middle fiber so that the distal ends of the fibers spread.

The above referred to devices use three optical fibers which can be manipulated to spread out within the interior of the body cavity being treated. Access to a body cavity, such as the uterus, for example, is via a relatively narrow opening, through which the devices must be manipulated. The width of devices which are composed of several fibers may be greater than the opening, thereby possible causing discomfort to the patient when being inserted. Since it is desired that treatment be carried out as a local or office procedure without general anesthesia, it is preferable that the device be as narrow as possible.

SUMMARY OF THE INVENTION

The present invention provides a system and method including a device utilizing a single optical fiber which can be manipulated within the body cavity so as to comprehensively treat the body cavity. A feature of the present invention is a device which can be controlled both longitudinally and laterally.

A further feature of the present invention is a second optic fiber for visualizing the cavity being treated which can be used in combination with the treatment fiber.

There is thus provided, in accordance with a preferred embodiment of the present invention, a device for manipulating movement within a body cavity which includes an optical fiber coupled to an energy source and a sleeve for containing the fiber. The fiber has distal end for positioning adjacent to the surface being treated and a proximal end located external to the body cavity which is coupled to an operating device for controlling the lateral and/or longitudinal movement of the fiber.

The optical fiber used for treatment may be a single induced interstitial thermotherapy (ITT) fiber.

Furthermore, in accordance with a preferred embodiment of the present invention, the lateral movement includes a plurality of stepped movements wherein after each step the operating device is activatable for a pre-determined period of time.

Furthermore, in accordance with a preferred embodiment of the present invention, the optical fiber has a variable cross-section for emitting a variable intensity of light or a uniform cross-section emitting a constant intensity of light. The optical fiber may be enclosed within a disposable sterile cover.

Furthermore, in accordance with a preferred embodiment of the present invention, a second optical fiber is included having a distal end for positioning adjacent to the surface being treated and a proximal end located external to the body cavity which is coupled to a light energy source. The second optical fiber is linked with the first optical fiber and the movement of the first and second optical fibers is synchronized.

In addition, in accordance with a preferred embodiment of the present invention, the lateral and/or longitudinal movement is either fixed, manually operated or operated by a motor coupled to the sleeve.

Furthermore, in accordance with a preferred embodiment of the present invention, the operating device includes a handpiece adapted to hold the proximal end of the optical fiber for controlling the lateral and/or longitudinal movement of the sleeve.

Additionally, there is provided, in accordance with a preferred embodiment of the present invention, a system for treating a body cavity. The system includes a light emitting source, an optical fiber for directing light from the light emitting source within the body cavity and an operating device connected to the sleeve for controlling at least the lateral movement of the sleeve thereby to correspondingly control the movement of the fiber.

The light emitting source is a laser or an incoherent light source.

In addition, there is also provided, in accordance with a preferred embodiment of the present invention a method for manipulating an optical fiber within a body cavity. The optical fiber has a distal end for positioning within the body cavity and a proximal end located external to the body cavity which is coupled to a energy source. The method includes the steps of:

inserting the optical fiber within a sleeve;
connecting the sleeve to an operating device; and
controlling the movement of the operating device thereby to control the movement of the sleeve and to corresponding control the movement of the distal end of the optical fiber within the body cavity. The movement is either lateral and/or longitudinal.

The step of controlling the movement includes the step of manually adjusting the operating device or coupling a motor to the sleeve and controlling the movement by adapting the motor to perform a pre-determined movement pattern.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
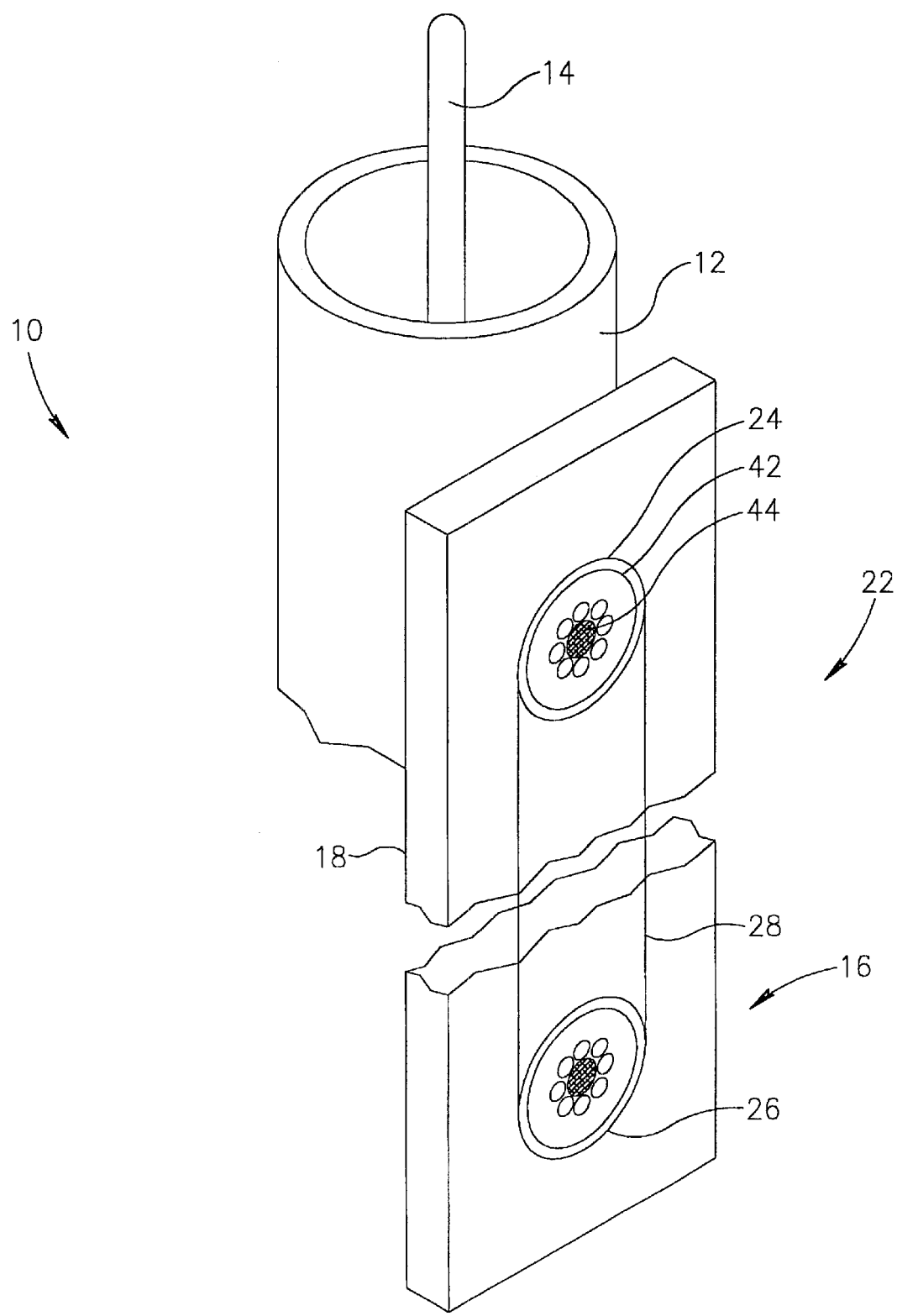
FIG. 1 is an isometric view of the movement control device constructed in accordance with a preferred embodiment of the present invention.

Reference is now made to FIG. 1, which is an isometric view (shown schematically for clarity) of a movement control device, generally designated 10, for the movement control in the interior of body cavities constructed in accordance with a preferred embodiment of the present invention. The movement control device, generally referenced 10, controls the movement of an optical fiber 14 which guides light from a light emitting source, such as a laser or an incoherent light source (not shown in FIG. 1), to the interior of a body cavity.

The movement control device 10 comprises two elements, namely a sleeve 12 which contains the fiber 14 and an operating device, generally designated 16 for controlling the movement of the sleeve 12 and hence the fiber 14 therewithin. Operating device 16 comprises a support element 18 and a pulley arrangement generally designated 22 and comprising pulleys 24 and 26 connected by cable 28.

In a preferred embodiment, the operating device 16 comprises a torque motor 20 (not shown in FIG. 1, to be discussed in connection with FIG. 2), which is coupled, via the pulley arrangement 22, to sleeve 12. The movement control device 10 further comprises a support element 18 which is disposed between the sleeve 12 and pulley arrangement 22 for housing and supporting motor 20 and pivotally supporting sleeve 12 and pulley arrangement 22.

The pulley arrangement 22 includes a pair of grooved pulleys 24 and 26 connected by piano cable wire 28 or similar high tensile cables or material.

Figure 2:
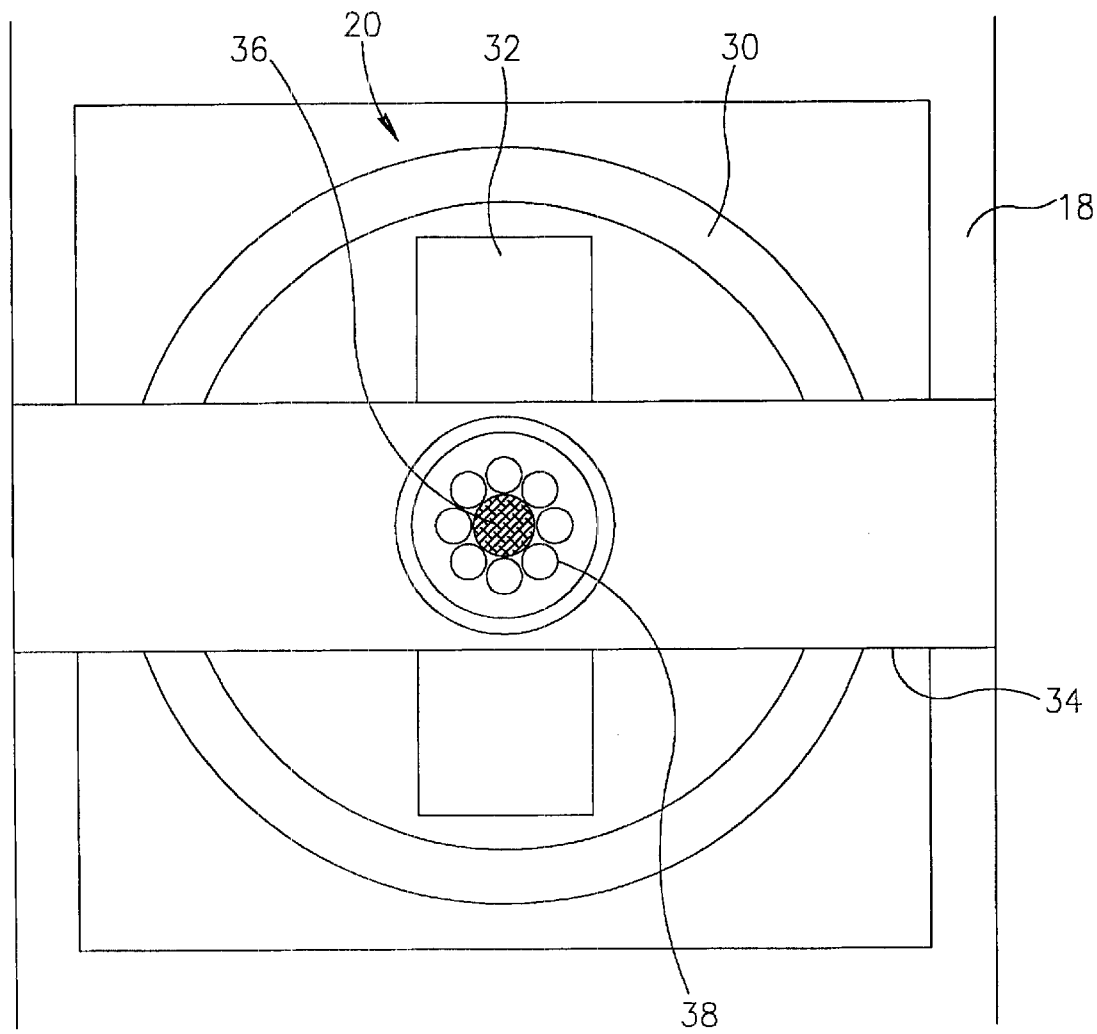
FIG. 2 is enlarged rear view elevation of part of the operating device of the movement control device of FIG. 1.

Reference is now also made to FIG. 2, which is an enlarged rear view elevation of part of operating device 16. Motor 20 comprises a fixed element 30 and a movable element 32. At least one strut 34 is attached to support element 18. Each of the struts 34 contain a ball bearing (referenced 38, respectively). Pivot pin 36 (also visible in FIG. 1) inserted within ball bearings 38 connects fixed element 30 with pulley 26, thus allowing pulley 26 to freely rotate.

Referring again to FIG. 1, support element 18 further comprises a ball bearing arrangement 42 retained therein. A second pivot pin 44 inserted within ball bearing arrangement 42 connects sleeve 12 with pulley 24, allowing pulley 24 and hence sleeve 12 to freely rotate about the axis of pivot pin 44.

Since pulleys 24 and 26 are connected by piano wire 28, movement actuated by motor 20 causes pulley 26 to rotate which causes a corresponding movement in pulley 24.

The motor 20 is electrically controlled and can provide the fiber 14 with any lateral movement pattern, as required.

In an alternative embodiment, operating device 16 is manually operated by an operator adjusting the pulley arrangement 22 in order to control the rotational movement of the sleeve 12.

For either manually or motor operated devices, preferably a spring mechanism or similar device (not shown) is connected to the sleeve 12 so that the sleeve 12 returns to its default position, which for example may be parallel to support element 18 (as shown in FIG. 1).

It will be appreciated that the optical fiber 14 may be used for treatment or viewing purposes.

In an alternative embodiment, operating device 16 (of FIG. 1) may optionally further comprise a second optical fiber coupled to a light source which is linked to the first optical fiber 14 so that their movement is synchronized. In this case, the first optical fiber 14 is configured for treating the patient while the second optical fiber is used for viewing the area being treated.

Figure 3:
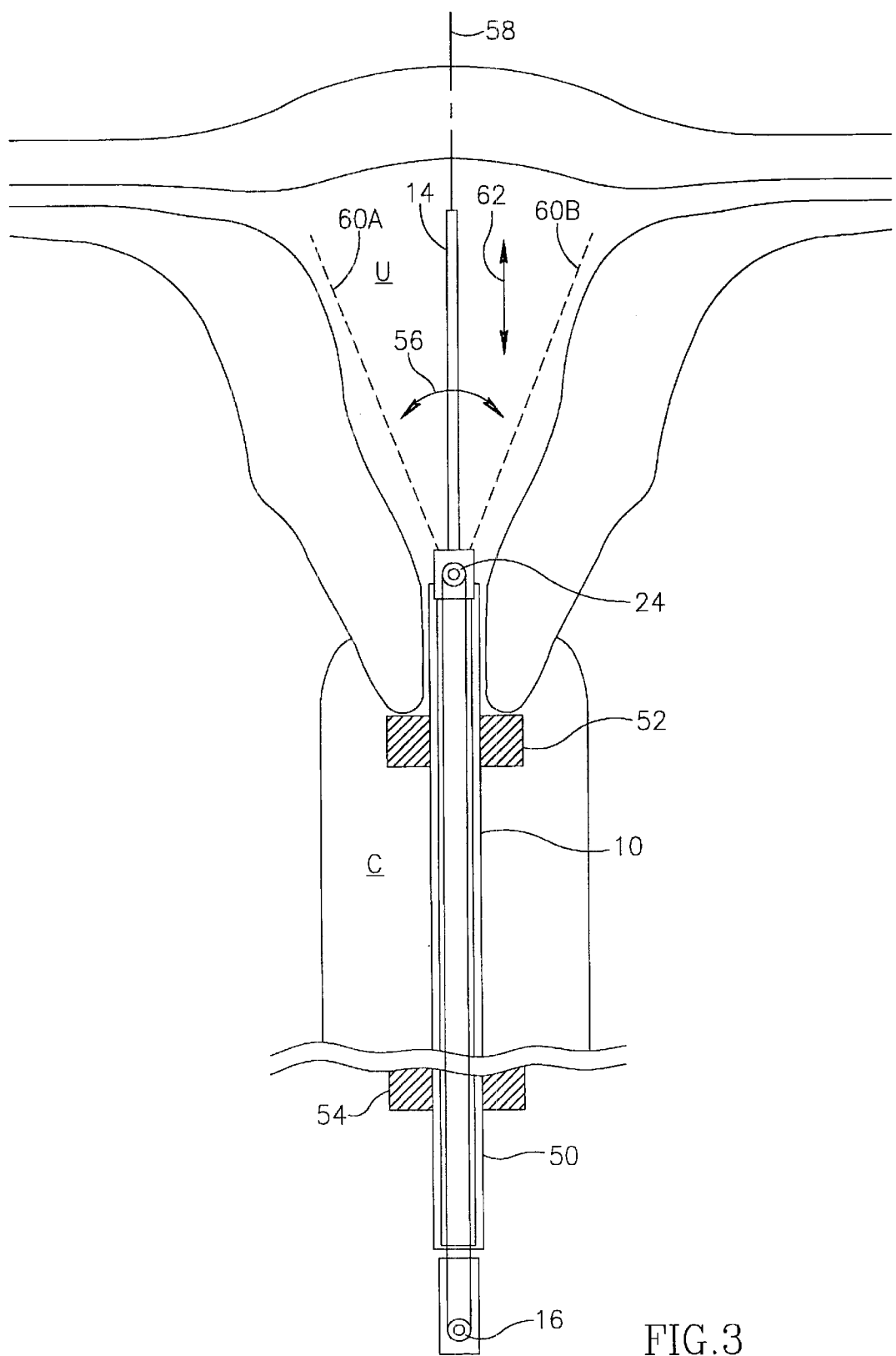
FIG. 3 illustrates the use of the movement control device of FIG. 1 in treating chronic menorrhagia.

Reference is now made to FIG. 3 which illustrates the exemplary use of movement control device 10 in treating chronic menorrhagia.

The movement control device 10 is inserted within a cannula 50, the distal end of which is inserted via the patient's vagina and cervix C into the uterus U, while the other end of the cannula 50 is outside the patient's body. Preferably, a ring 52 is fitted to the distal end of the cannula 50 to limit entry of the cannula against the mouth of the uterus U. Optionally a second ring 54 is fitted to the middle of the cannula 50 to limit the cannula against the mouth of the cervix C.

The operating device 16 is located external to the cannula 50 and as described hereinabove may be moved rotationally either by a motor or manually.

A single optical fiber 14 is disposed within the movable sleeve 12 and extends through cannula 50. Optionally, a second optical fiber, which is coupled to a light source for viewing purpose, may be suitably linked to optical fiber 14. The following description describes the use of a single optical fiber for the purposes of example only, but it will be appreciated that one or two fibers may be used and disposed within the cannula 50.

The proximal end of the optical fiber 14 is located externally from the patient's body and is coupled to a source of laser energy. The distal end of the optical fiber 14 is located within the uterus U when the device is being used.

Preferably, the optical fiber 14 is enclosed within a disposable sterile cover (not shown) which is translucent to the radiation being emitted from the fiber 14.

In an alternative preferred embodiment, the distal end of the optical fiber 14 can be adapted, by roughening the surface or adding grooves, for example, to control the intensity of the emitting light along its longitudinal length and azimuth, as described in the Applicants corresponding U.S. application Ser. No. 09/050,788, incorporated herein by reference. Various grooves with different shape, depth, orientation and density, for example, can be imposed on the surface to affect the scattered light intensity distribution.

To treat the patient, the cannula 50 is inserted into the patient's uterus U via the cervix C, being limited in its movement by the rings 52 and 54. In this position, the sleeve 12 is positioned just inside the neck of uterus U so that it free to move laterally, indicated by arrow 56. Thus, sleeve 12 (and hence optical fiber 14) can be moved from its exemplary default position (indicated by center line 58) approximately 45 degrees either side thereof (indicated by dashed lines 60a and 60b) to cover the lateral width of the uterus.

It will be appreciated that the optical fiber 14 is flexible, and so any exaggerated movement of the sleeve 12 will cause the fiber 14 to bend at the point where it contacts the wall of the uterus and temporarily push the tip inwards towards the center line 58. However, this 'bending' will be corrected as the sleeve return back towards its default position.

In an alternative preferred embodiment, a second linear motor (or similar) can be connected to the proximal end of the optical fiber 14 to longitudinally adjust the optical fiber 14 (indicated by arrow 62). The motor 20 is electrically controlled to allow the fiber 14 to move in accordance with any longitudinal pattern, as required.

The option of longitudinal movement allows the operator to utilize a fiber having a uniform cross-section emitting a constant intensity of light. The intensity of emitted light can alternatively be controlled by adjusting the power input to the optical fiber 14, as a function of time and location, so that, for example, less power is used for sensitive areas near the cervix.

The operation of the torque motor (for lateral movement) and the linear motor (for longitudinal movement) can be synchronized together so as to treat and/or view the whole uterus, adjusting the movement of the motors and power intensity, as a function of time and location, to a predetermined program.

In an further alternative preferred embodiment, the optical fiber 14 can be moved both laterally and longitudinally by manually adjusting the optical fiber 14.

Figure 4:
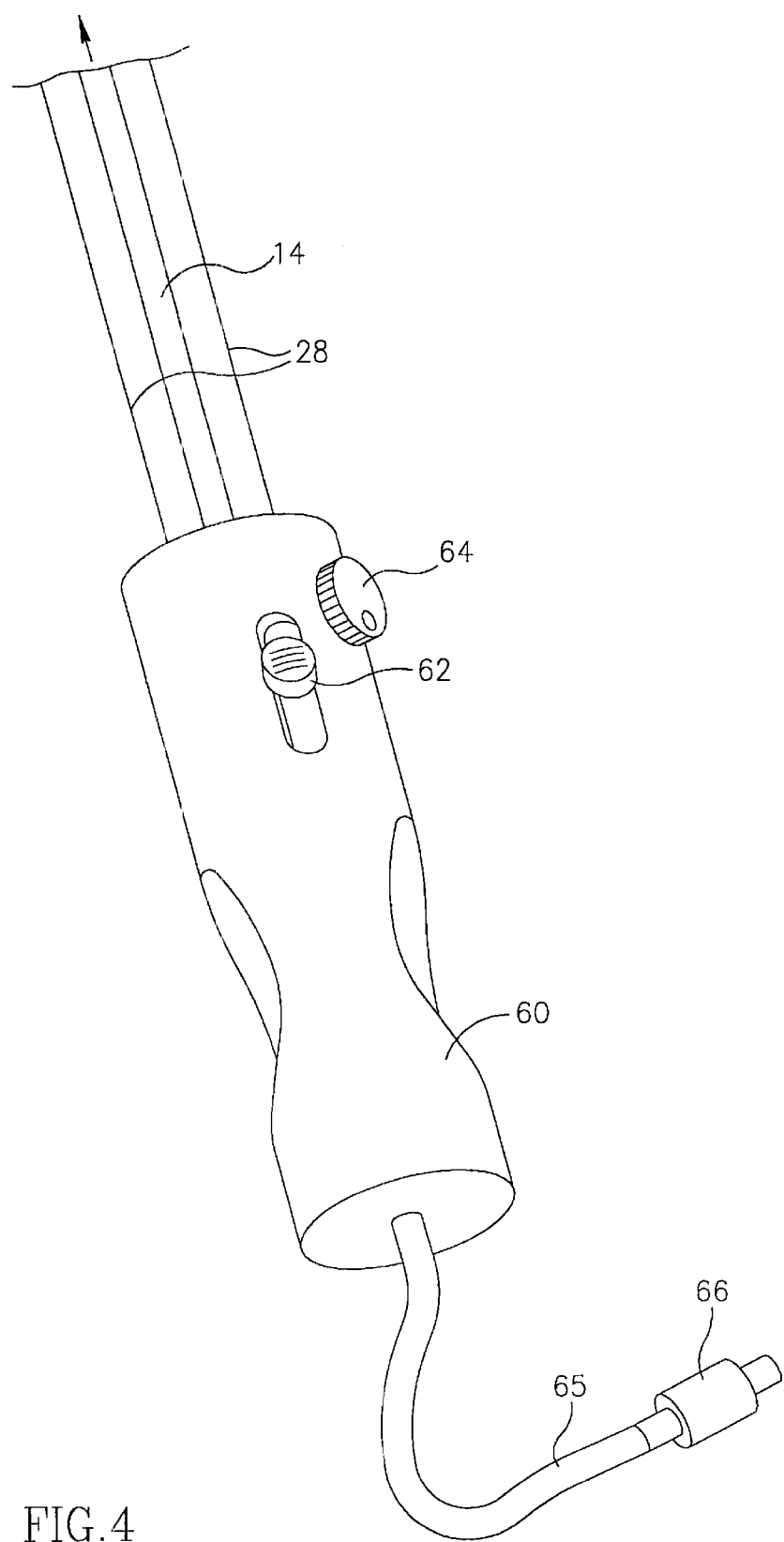
FIG. 4 is an isometric view of a handpiece used in combination with the device of FIG. 1.

FIG. 4, to which reference is now made, illustrates a manually operated handpiece 60 adapted to bold the proximal end of at least one optical fiber, such as treatment fiber 14. Elements of this embodiment of the invention which are similar to elements which have been previously described with respect to the preferred embodiment hereinabove, are similarly designated and will not be further described.

Handpiece 60 further comprises a pulley (not shown but similar to pulley 26 and referenced 126 in the text only, for clarity) connected by piano wire 28 to a second pulley 24 (described hereinabove with respect to FIG. 1). The handpiece 60 further includes a push/pull lever mechanism 62 for pushing/pulling the laser fiber 14 so as to apply a longitudinal movement at the fiber's distal end within the uterus and a knob 64 for rotating the pulley 126 within the handpiece. Since pulleys 126 and 24 are connected by piano cable wire 28, movement actuated by the rotation of pulley 126 causes pulley 24 to rotate which causes a lateral movement in sleeve 12.

At its proximal end 65, the optical fiber 14 is terminated with standard fiber connectors 66, connected to a light source (not shown), such as a laser.

A second optic laser fiber can be linked with the treatment fiber 14 into a single unit to allow the handpiece to be used for treatment and/or viewing.

It will be appreciated that the lateral and longitudinal movements can be applied by a combination of motor and manual control, as well as fixed movement in one of the directions. This is illustrated by the following exemplary table:

|  | | LATERAL Movement | | |
| --- | --- | --- | --- | --- |
|  |  | Motor Control | Manual Control | Fixed |
| LONGI-TUDINAL Movement | Motor Control | ✓1 | ✓2 | ✓3 |
|  | Manual Control | ✓4 | ✓5 | ✓6 |
|  | Fixed | ✓7 | ✓8 | ✓9 |

Thus, there are nine possible combinations of lateral and longitudinal movement control, as indicated by the symbol "✓". For example, the lateral movement can be controlled by motor and the longitudinal movement controlled manually (example 4) or the longitudinal movement can be motor controlled and with a fixed lateral movement (example 3).

The motorized device can be adapted to function in an "automatic" mode so that it moves laterally across the uterus, for example (FIG. 3), in three defined steps, at each position resting for a pre-determined time, for treatment at that position.

It will be further appreciated by persons skilled in the art that the present invention is not limited to the treatment of uterine tissue but the device may be utilized to treat any tissue volume.

While the invention has been described with respect to one preferred embodiment, it will be appreciated that this is set forth merely for purposes of example, and that many other variations, modifications and applications of the invention may be made.

We claim:

1. A method for manipulating an optical fiber within a uterus, said optical fiber having a distal end for positioning within said uterus and a proximal end located external to said uterus which is coupled to an energy source, said method comprising the steps of:

inserting said optical fiber within a sleeve;

delivering radiation through said fiber for coagulation of the lining tissue of the uterus; and controlling said operating device thereby to control the movement of said sleeve and to correspondingly control the movement of the distal end of said optical fiber within the uterus;

wherein said movement is lateral and/or longitudinal movement; and wherein the step of controlling the movement comprises the step of adapting said motor to perform a pre-determined movement pattern.

* * * * *